United States Patent [19]

Makler

[11] Patent Number: 5,124,141
[45] Date of Patent: Jun. 23, 1992

[54] METHOD FOR DIAGNOSING MALARIA

[75] Inventor: Michael T. Makler, Portland, Oreg.

[73] Assignee: Flow Incorporated, Portland, Oreg.

[21] Appl. No.: 538,126

[22] Filed: Jun. 14, 1990

[51] Int. Cl.$^5$ .................. G01N 33/15; G01N 31/00; C12Q 1/32; C12Q 1/28

[52] U.S. Cl. .................. 424/7.1; 424/9; 435/26; 435/28; 435/190; 435/808; 436/94; 514/44

[58] Field of Search .................. 424/7.1, 9; 435/26, 435/28, 190, 808; 436/94; 514/44

[56] References Cited

U.S. PATENT DOCUMENTS

| Re. 32,016 | 10/1985 | Esders et al. | 435/28 |
| 4,080,263 | 3/1978 | Bernt et al. | 435/16 |
| 4,097,338 | 6/1988 | Konttinen | 435/26 |

OTHER PUBLICATIONS

Kaplan, N. O. et al., "Chemistry and Properties of the 3-Acetylpyridine Analogue of Diphosphopyridine Nucleotide," *Journal of Biochemistry*, 221:823-832 (1956).
Vanderjagt, D. L. et al., "Partial Purification and Characterization of Lactate Dehydrogenase from Plasmodium Falciparum," *Molecular and Biochemical Parasitology*, 4:255-264 (1981).
Sherman, I. W., "Biochemistry of Plasmodium (Malarial Parasites)", *Microbiological Reviews*, (1979) pp. 464-466.
Sherman, I. W., "Heterogeneity of Lactic Dehydrogenase in Avian Malaria Demonstrated by the Use of Coenzyme Analogs" (Abstract), *Proceedings of First International Congress of Parasitology*, p. 73(a) (1966).
Bhat, I. K. et al. Res. Vet. Sci. 42(1):127-9 (1987).
Tanabe, K. J. Protozool. 30(4):707-710 (1983).
Burlina, A. Methods Enzym. Anal. 7:34-38 (1985).
Niekamp, C. W. et al. Biochemistry 19:3144-3152 (1980).
Makler, M. T. et al. Cytometery 8:568-570 (1987).
Kandel, J. et al. J. Biol. Chem. 249(7):2088-2097 (1974).

Primary Examiner—Richard L. Raymond
Assistant Examiner—Gary E. Hollinden
Attorney, Agent, or Firm—Kolish, Hartwell, Dickinson, McCormack & Heuser

[57] ABSTRACT

A diagnostic method for the detection of human malaria infections. Specifically, blood samples are combined with a reagent containing 3-acetyl pyridine adenine dinucleotide (APAD), a substrate (e.g. a lactate salt or lactic acid), and a buffer. The reagent is designed to detect the presence of a unique glycolytic enzyme produced by the malaria parasite. This enzyme is known as parasite lactic acid dehydrogenase (PLDH). PLDH is readily distinguishable from host LDH using the foregoing reagent. Combination of the reagent with a parasitized blood sample results in the reduction of APAD. However, APAD is not reduced by host LDH. The reduced APAD may then be detected by various techniques, including spectral, fluorimetric, electrophoretic, or colorimetric analysis. Detection of the reduced APAD in the foregoing manner provides a positive indication of malaria infection.

15 Claims, 3 Drawing Sheets

SPECTROPHOTOMETRIC ANALYSIS OF CRBC AND PRBC

ISOENZYMES OF LACTATE DEHYDROGENASE

| NAD | | | | | APAD | | | |
|---|---|---|---|---|---|---|---|---|
| C | P | C | P | | C | P | C | P |
| ▬ | ▬ | ▬ | ▬ | | — | — | — | — |
| ▬ | ▬ | ▬ | ▬ | | — | — | — | — |
| ▬ | ▬ | ▬ | ▬ | | — | — | — | — |
| | | | ▬ | | | ▬ | | ▬ |

▬ STAINED

— UNSTAINED
  AND ACTUALLY NOT SEEN IN ELECTROPHOROGRAM

FIG. 3A  FIG. 3B 5,124,141

METHOD FOR DIAGNOSING MALARIA

BACKGROUND OF THE INVENTION

The present invention generally relates to a method for diagnosing malaria, and more particularly to a highly specific diagnosis method based on the detection of malaria parasite glycolytic enzymes.

Malaria is one of the most wide-spread infectious diseases. The World Health Organization estimates that 200,000,000 people are infected with the malaria parasite annually. These people mainly reside in the tropics. One million cases of malaria were reported in the United States in 1940. At that time, effective measures were introduced which virtually eliminated the disease, which is transmitted by the female Anopheles mosquito. However, the Anopheles mosquito is still present in many of the Southern and Western parts of the United States. During the early 1970's, there were several cases of malaria reported in Louisiana and California. These were attributed to returning veterans from the Viet Nam war who harbored the parasite.

As tropical regions of the world become more accessible through improved modes of transportation, travel into these areas is increasing. This has resulted in significantly more cases of malaria being reported in travelers returning from these areas. One percent (1%) of all people infected with the malaria parasite die from the disease. Specifically, in 1989, 2,700,000 people died of malaria. There are four species of Plasmodium which infect humans and cause malaria. These include *P. falciparum*, *P. vivax*, *P. ovale*, and *P. malariae*. *P. falciparum* is the most serious species. It is responsible for cerebral malaria which is associated with a 50% mortality rate.

There are now over 65 countries which have reported chloroquine-resistant *P. falciparum*, and 12 countries which have reported quinine-resistant *P. falciparum*. These two anti-malarial drugs were the major therapeutic agents used to treat the disease, and their indiscriminate use has added to the spread of resistant strains of malaria parasite. Since these drugs are rapidly becoming entirely or partially ineffective for specific parasite species, it is essential that an accurate diagnosis of the disease be obtained in order to provide proper treatment. The diagnostic method of choice must be rapid, specific, readily available, easy to perform, and easy to interpret.

The life cycle of a Plasmodium parasite involves the interrelationship between an Anopheles mosquito vector and a mammalian host. When an uninfected female Anopheles mosquito bites and ingests blood from a host harboring the sexual forms of the Plasmodium parasite, the parasitic life cycle begins. In the Anopheles, the male and female gametocytes fuse and travel after several stages of development to the salivary glands of the mosquito. The parasite at this stage is called a "sporozoite." If the infected mosquito bites a new host, the sporozoites are injected into the host's blood. Thereafter, they travel to the liver within 30 minutes, where they enter a liver cell. In the liver cell, one sporozoite multiplies and forms about 10,000-20,000 merozoites. These merozoites are released from the liver cells in 10-12 days. Each of the released merozoites immediately invades an erythrocyte. In 48 hours, each merozoite forms another 10-12 merozoites which are in turn released from the erythrocyte only to invade another 10-12 erythrocytes.

The clinical manifestations of the disease include fever, headaches, sweating, vomiting, and prostration. These manifestations occur simultaneously with merozoite release from the erythrocytes. The erythrocyte reinvasion occurs until the host dies, or until the host's immune system is able to control and suppress merozoite activity. At some point, the merozoites (previously asexual) differentiate into male and female gametocytes. The technical and scientific basis for this transformation is an active area of current medical research. If a female Anopheles then bites a new host at the time of gametocyte formation, the life cycle of the parasite is completed.

The most susceptible human hosts for the disease are infants and pregnant women having suppressed immunity. Recently, deaths have been reported in adult male AIDS patients caused by cerebral malaria. In addition, non-immune travelers into high-risk malaria areas are also susceptible to the disease, especially with respect to chloroquine and quinine resistant malaria.

There is a natural immunity to malaria which develops in persons living in high-risk malaria areas. This immunity appears to depend upon the continual presence of low parasite levels in the host's body. This conclusion is drawn from many studies which demonstrate that when persons living in high-risk malaria areas leave and travel to low-risk areas, they substantially lose their immunity.

As previously mentioned, the disease must first be properly diagnosed before treatment may be given. Ideal diagnostic methods must be specific, sensitive, accurate, easy to implement, and require a minimum of complex diagnostic equipment. Numerous approaches have been taken regarding the laboratory diagnosis of malaria. These approaches include the use of thick and thin blood smears treated with a conventional stain known as "Giemsa" and examined with a light microscope. Other methods range from fluorescent dyes to recently developed methods involving DNA probes, indirect fluorescent antibody tests, indirect haemagglutination tests, enzyme-linked immunosorbent assays, and gel precipitation tests as extensively discussed in *Bulletin of the World Health Organization: Malaria Diagnosis*, 1045, 1–37 (1988).

With respect to other malaria diagnostic procedures, U.S. Pat. No. 3,834,874 to Geating et al. involves a Plasmodia detecting apparatus consisting of a pre-stained microscope slide covered with a dried mixture of methylene blue NN and cresyl violet acetate.

Australian patent application 66/04,418 discloses a blood smear composition comprising a solution of methylene blue chloride, an alkali metal bicarbonate (preferably $NaHCO_3$), eosin Y, and azure (II)-eosin in an alcohol mixture. The resulting composition is designed to detect malaria parasites and may be used for all types of blood smears (thick and thin). A similar process is disclosed in British Patent 1,183,499 which involves a biological stain for detecting malaria in which a blood film is first stained with polychrome methylene blue solution, followed by treatment with an eosin solution.

U.S. Pat. No. 4,741,898 discloses a stabilized Romanowsky-type stain composition for malaria parasites which includes a cationic dye component (methylene blue, azure A, azure B, azure C, or thionin), an anionic dye component (eosin Y, eosin B, fluorescein, substituted fluorescein, or orange G), a 1-6 carbon alcohol solvent, and a stabilizer (e.g. lysine or glycine).

Further information regarding malaria staining techniques is disclosed in Bianco, A. E. et al., "Plasmodium Falciparum: Rapid Quantification of Paracitemia in Fixed Malarial Cultures by Flow Cyctometry", *Exp. Parasitol.*, 62:75-282 (1986); Tanabe, K., "Staining of *Plasmodium Yeoli*-Infected Mouse Erythrocytes with the Fluorescent Dye Rhodamine 123", *J. Protozool.*, 30:707-710 (1983); Makler, M. T. et al., "Thiazole Orange: A New Dye for Plasmodium Species Analysis", *Cytometry*, 8:568-570 (1987); and Patton, C. L. et al., "Diagnosis of Malaria Using Quantitative Buffy Coat (QBC TM)", Documents Complementaires: Resume of 3rd International Conference on Malaria and Babesiosis, Annecy 1987.

The article by Makler, M. T. et al. is of particular interest in that it discloses a fluorescent staining technique for *Plasmodium falciparum* using a membrane-permeable fluorochrome thiazole orange dye in conjunction with a fluorescent flow cytometer.

A variety of other diagnosis methods exist for detecting the presence of malaria infections. For example, French patent application 2,572,528 involves a process for identifying, sorting, and counting microscopic particles (including Plasmodia) in which test samples are first prepared and deposited in succession on an advancing conveyor surface. The conveyor surface moves the samples into the viewing field of a microscope providing images which are recorded by a video camera. The recorded images are then set against a squared pattern grid so that the image corresponding to each sample may be analyzed according to standard pattern recognition techniques.

European patent application 119,209 involves a method for identifying microorganisms including malaria parasites through the use of DNA probes. The parasites are first immobilized on a solid support. DNA from the parasite sample is then subjected to hybridization with a labeled specimen of species-specific, non-cross hybridizing DNA from a known species. The parasite sample is then examined for hybridization between the first and second DNA materials.

Canadian Patent 951,242 involves an immunoglobin M diagnostic reagent for detecting malaria and other diseases consisting of polystyrene particles coated with IgM. To determine IgM levels in a sample of test serum and detect disease infestation, the serum is first mixed with human IgM antiserum followed by combination with the polystyrene-IgM reagent. If agglutination occurs, IgM levels are normal and there is no disease.

Australian patent application 87/72,041 discloses a method in which nucleotide sequences from the RESA antigen of *Plasmodium falciparum* are used as detection probes.

Notwithstanding the methods described above, a need exists for a malaria diagnosis procedure which is easily used, requires minimal amounts of instrumentation, and is parasite sensitive and specific. The method must be economical, and capable of providing accurate test readings in remote geographical regions. The present invention satisfies these goals, and represents an advance in the field of disease diagnosis, as described below.

SUMMARY OF THE INVENTION

It is an object of the present invention to provide a diagnostic method for malaria which is characterized by a high degree of accuracy.

It is another object of the invention to provide a diagnostic method for malaria which is easy and economical to use.

It is a further object of the invention to provide a diagnostic method for malaria which requires minimal amounts of labor and equipment.

It is a further object of the invention to provide a diagnostic method for malaria which is readily adaptable for use in isolated geographical areas.

It is an even further object of the invention to provide a diagnostic method for malaria which is sensitive and specific, and which is capable of delivering rapid results.

It is a still further object of the invention to provide a diagnostic method for malaria which involves the use of a chemical detection system for glycolytic enzymes produced by the infecting parasites during disease manifestation.

In accordance with the foregoing objects, the present invention involves a unique and efficient method for detecting and diagnosing malaria in human subjects. The method involves the selective determination and characterization of parasite lactic acid dehydrogenase (PLDH) in blood samples. The parasite LDH is distinguishable from normal human erythrocyte LDH through the use of a specialized detecting reagent. The reagent consists of 3-acetyl pyridine adenine dinucleotide (APAD) in combination with a selected substrate (e.g. a lactate salt or lactic acid) and a buffer. Combination of the reagent with a sample of parasite-infected blood catalyzes oxidation of the substrate and simultaneously reduces the APAD. Host LDH has no influence on the APAD.

The reduced APAD may then be detected in numerous ways. For example, the reduced material may be spectrophotometrically detected by observing its characteristic absorption peak at about 363-365 nm, which is distinctive from the absorption spectra of a sample containing unreduced APAD. It is also possible to colorimetrically detect the reduced APAD using a series of chromogens. The chromogens (e.g. tetrazolium salts) react in the presence of the reduced APAD to generate a colored product which is visually detectible. Finally, the reduced APAD is fluorescent, and may be detected using an appropriately configured fluorescent lamp system or fluorometer. Regardless of which detecting method is used, the present invention enables the rapid and accurate detection of malaria-infected blood in a manner not heretofore known in the art.

These and other objects, features, and advantages of the invention shall be described below in the following Detailed Description of a Preferred Embodiment and Brief Description of the Drawings.

BRIEF DESCRIPTION OF THE DRAWINGS

FIGS. 3A (left) and 3B (right) are electrophorograms of uninfected control (C) human blood and parasite infected (P) human blood stained with nicotinamide adenine dinucleotide and 3-acetyl pyridine adenine dinucleotide, respectively.

DETAILED DESCRIPTION OF A PREFERRED EMBODIMENT

Figure 1:
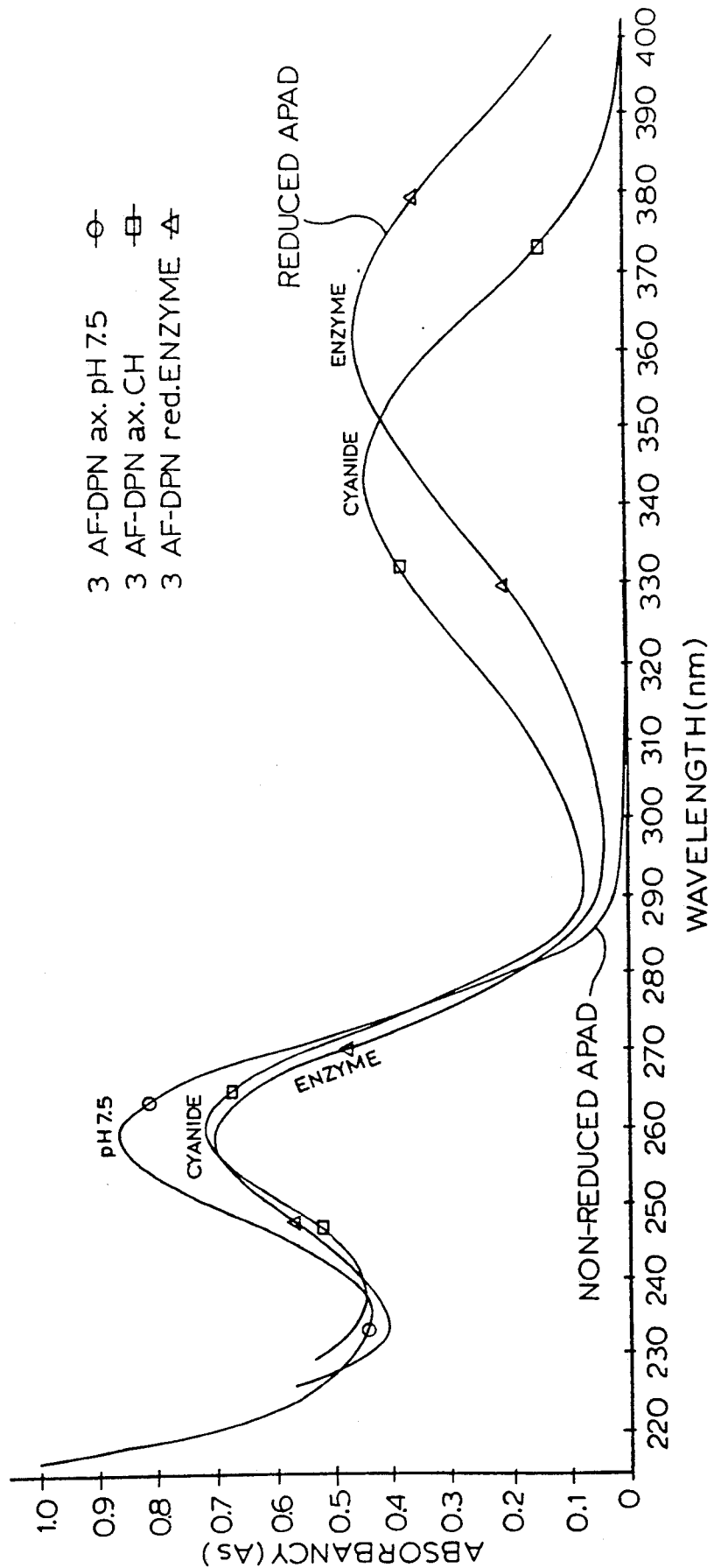
FIG. 1 is a comparative illustration of the spectrophotometric absorption peaks for reduced and nonreduced 3-acetyl pyridine adenine dinucleotide.

The present invention involves a unique and effective method for diagnosing malarial infections caused by *Plasmodium falciparum*. Specifically, blood samples are combined with a unique reagent which produces a chemical reaction in the presence of malaria-infected blood. This reaction is readily detectible using a variety of methods.

As previously indicated, a need remains for a practical and effective malaria diagnosis method. Other techniques currently in use (including Giemsa staining methods as previously discussed) are frequently inaccurate or require long periods of time for accurate diagnosis at low infection levels. In addition, these techniques are time consuming, labor intensive, and often require scientifically trained personnel. From a practical standpoint, an effective, sensitive and specific malaria diagnosis technique should not require the use of a microscope or other sophisticated equipment.

The present invention satisfies these goals, and is readily usable without extensive technical equipment or trained personnel. In general, the diagnosis method of the invention evaluates and detects the metabolic products of the malaria parasite. It then distinguishes these products from those generated by host erythrocytes so that malarial infections may be positively characterized.

Specifically, the method of the present invention depends upon the presence of a unique enzyme generated by the intracellular form of the malaria parasite. This enzyme consists of parasite lactic acid dehydrogenase (hereinafter "PLDH"). In the parasite, this enzyme is capable of catalyzing the conversion of pyruvate to lactate, or the reverse conversion of lactate to pyruvate. This catalysis depends on numerous factors, including pH and coenzyme concentrations. It is known in the scientific literature that PLDH differs in catalytic activity from the lactic acid dehydrogenase (hereinafter "LDH") produced by host (human) erythrocytes. Vanderjagt, D. L. et al., "Partial Purification and Characterization of Lactate Dehydrogenase From *Plasmodium falciparum*," *Molecular and Biochemical Parasitology*, 4:225-264 (1981).

To detect PLDH, a blood sample is first obtained. The term "blood sample" as used herein shall include but not be limited to samples of whole blood, blood hemolysates, plasma, serum or the like. For example, a hemolysate usable in connection with the present invention may be prepared from a sample of whole blood suspended in water in a 1:1 volume ratio. However, as noted above, the present invention shall not be limited to the use of blood hemolysates alone.

Thereafter the blood sample is combined with a specialized reagent produced in accordance with the present invention. This reagent includes three main components. The first component consists of 3-acetyl pyridine adenine dinucleotide (hereinafter "APAD") which has the following structure:

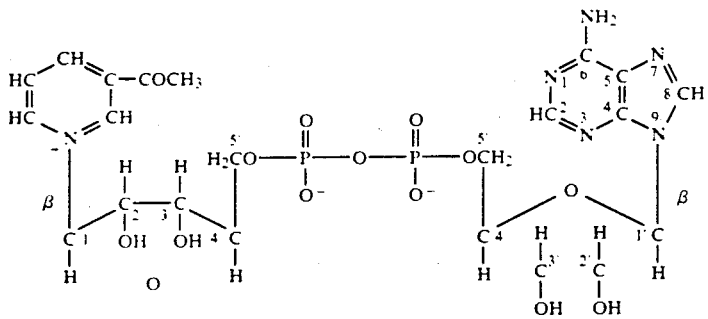

This material functions as a coenzyme/necessary cofactor in the reaction described herein, and is reduced enzymatically in the presence of PLDH. It is unaffected by host LDH. This material is commercially available from the Sigma Chemical Corporation of St. Louis, Mo.

Next, the reagent includes a substrate which is basically defined as a molecule whose chemical conversion is catalyzed by an enzyme. In a preferred embodiment, the substrate consists of a lactate salt such as lithium lactate, magnesium lactate, sodium lactate, calcium lactate, or other lactates listed on page 633 of the 1990 Sigma Chemical Corporation Catalog. Also, d,l-lactic acid may be used as the substrate. In other words, d,l-lactic acid or lactate salts may be used as substrates.

Finally, the reagent includes at least one buffer. The buffer functions to maintain the pH of the reagent at between about 8.0-10.0. Exemplary buffers include but are not limited to AMPSO ((3-[(1,1-Dimethyl-2-hydroxyethyl)amino]-2-hydroxypropanesulfonic acid); CHES (2N-cyclohexylaminoethane sulfonic acid); BIS TRIS PROPANE (1,3 bistrishydroxymethyl methylaminopropane), AMP (2-amino-2-methyl-1-propanol), TRIS (trishydroxymethylaminomethane) and other materials known in the art and listed on page 1496 of the 1990 Sigma Chemical Corporation Catalog.

In a preferred embodiment, the reagent will contain 0.01-10 mM APAD, 0.01-500 mM substrate, and 0.02-1.0M buffer.

The reagent and blood sample are then combined in a preferred sample:reagent volume ratio of about 1:300 if a hemolysate is used. If serum is used, the ratio could preferably range from about 1:1 to 1:20 (or any appropriate dilution as required). If the blood sample contains any parasites (and PLDH), the APAD is enzymatically reduced (the reduced APAD being hereinafter termed "APADH"). Also, the substrate is oxidized (e.g. lactate to pyruvate as in the following reaction):

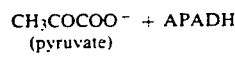

The APADH may thereafter be detected be detected in three main ways. First, the APADH may be detected using spectrophotometric techniques. As noted above, the presence of PLDH causes oxidation of the substrate and simultaneous reduction of the APAD. The presence of reduced APAD (APADH) is detected by its characteristic absorption peak at 363-365 nm. Additional information regarding this analytical technique will be described below in Example 2.

Second, it is also possible to demonstrate the presence of PLDH colorimetrically. Reduction of the APAD to APADH can cause the corresponding reduction of a chromogen (e.g. nitro blue tetrazolium or a general class of tetrazolium salts) to produce a visibly colored reaction. More information regarding this technique is discussed below in Example 3.

Third, PLDH may be detected fluorimetrically. APADH is inherently fluorescent, and can be detected directly using a fluorescent lamp known in the art (e.g. long wave ultraviolet—excitation at 375 nm; emission at 440-480 nm). More information regarding this technique is discussed below in Example 4.

Finally, the presence of PLDH may be demonstrated electrophoretically with the use of the reagent, as described in Example 5.

The following Examples provide additional specific information regarding the materials and methods of the present invention:

EXAMPLE 1

In this Example, parasitized blood was combined with a reagent produced as described herein. The parasitized blood was infected with *Plasmodium falciparum* (e.g. ATCC Nos. 50005, 50028, 30998, or 30992). The blood had a parasitemia rate of about 10% (e.g. about 10% of the individual cells were infected with parasites). In this Example, a hemolysate was prepared by combining whole blood with water in a 1:1 volume ratio. Thereafter, 300 ml of the reagent was prepared by combining 68 mg of APAD, 0.720 g of lithium lactate, and 3.633 g of TRIS buffer (pH adjusted to 9.0 with HCl). The resulting reagent had a concentration of 0.33 mM APAD (0.023% by weight), 25 mM lithium lactate (0.24% by weight), and 0.1M buffer (1.211% by weight). The final pH of the reagent was approximately 9.0. Thereafter, 10.0 microliters of hemolysate were combined with 3.0 ml of reagent to produce an individual test sample. In this sample, APAD was reduced to APADH due to the presence of PLDH.

As a control, a non-parasitized blood hemolysate was combined with the foregoing reagent using the same quantities, proportions, and materials described above. After reagent treatment, both samples were analyzed as described below in Examples 2-5.

EXAMPLE 2

Figure 2A:
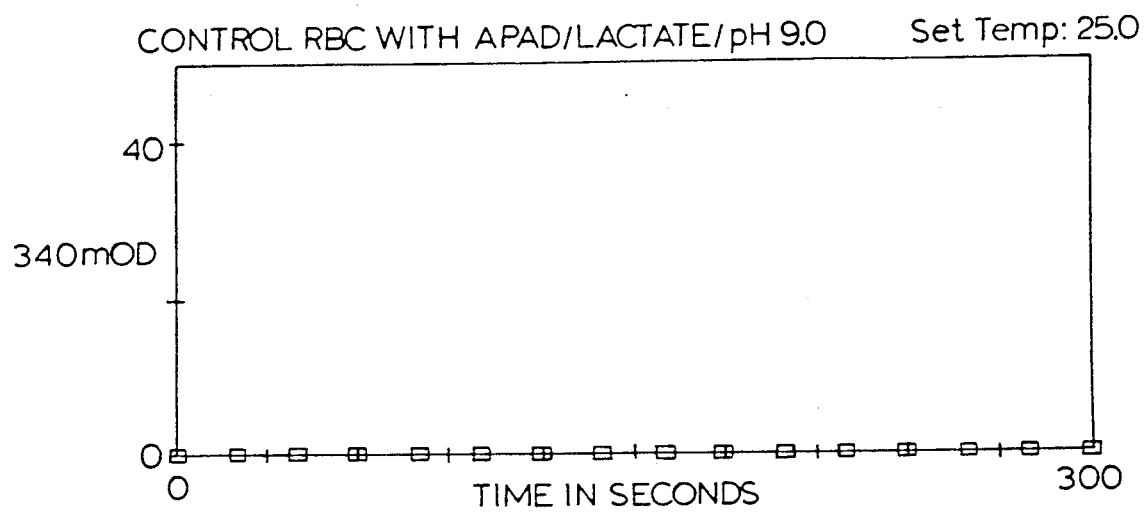
FIG. 2A is the OD 340 nm change of control erythrocytes incubated with APAD, lactate, and buffer (APAD reagent).
Figure 2B:
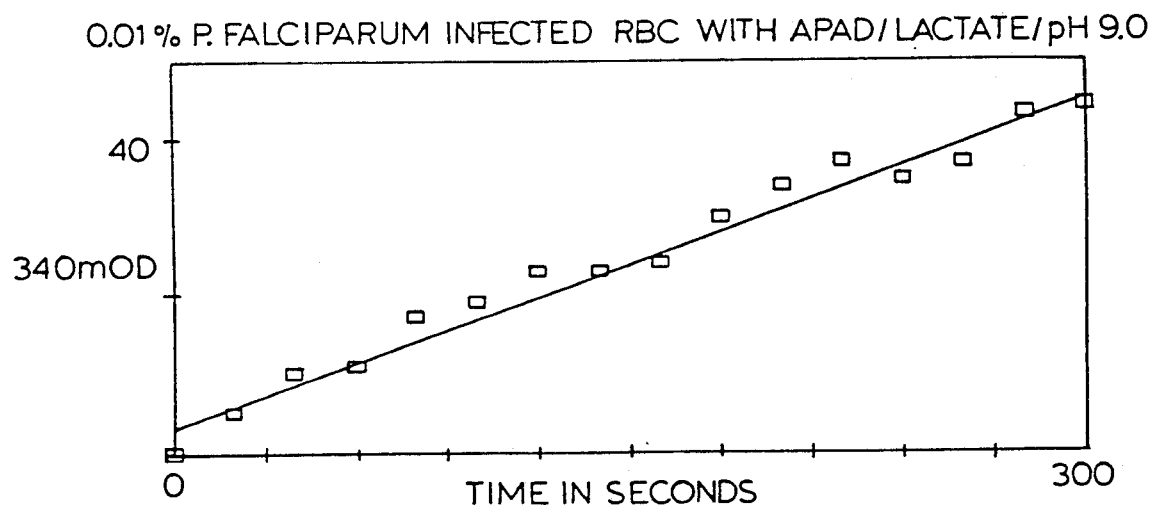
FIG. 2B is the OD 340 nm of human parasite infected blood incubated with the same APAD reagent.

In this Example, samples of reagent-treated hemolysate prepared as described above (parasitized and non-parasitized) were placed in a spectrophotometer (Shimazu Co., model 160) with the wavelength set at or near the absorption peak of APADH (340-380 nm). The parasitized sample had a characteristic absorption peak at about 363-365 nm, while the non-parasitized sample did not. FIG. 1 illustrates the characteristic absorption peak of reduced APAD compared with non-reduced APAD. These results clearly indicate that PLDH and host LDH may be readily distinguished in accordance with the invention, thereby allowing malaria infections to be rapidly diagnosed. FIG. 2A is OD 340 nm change of control erythrocytes incubated with APAD, lactate, and buffer (APAD reagent). FIG. 2B is OD 340 nm of human parasite infected blood incubated with the same APAD reagent. Notice in the control human blood (2A) there is no significant change of OD 340 nm compared to 2B.

EXAMPLE 3

In this Example, samples of hemolysate prepared as described above in Example 1 (parasitized and non-parasitized) were combined with the following chromogen: 0.15 mg nitro blue tetrazolium (2,2' di-p-nitrophenyl-5,5'-diphenyl-3,3',3,3',-dimethoxy-4,4'-diphenylene ditetrazolium chloride). In addition, 0.0075 mg phenazine methosulfate (N-methyldibenzopyrazine methyl sulfate salt) was added. The resulting mixture had a concentration of 0.33 mM APAD, 25 mM lithium lactate, 0.1M buffer, 0.24 mM nitro blue tetrazolium, and 33 $\mu$M phenazine methosulfate (PMS). The phenazine methosulfate functions as a reaction catalyst, while the nitro blue tetrazolium is designed to receive a hydrogen ion from the ADAPH, causing a color change. The mixture was allowed to stand for about 1.0 hr. at room temperature (about 24 degrees C.). A characteristic blue color developed in the parasitized sample, while a blue color was not produced in the non-parasitized sample. If desired, the amount of blue color (indicating the presence of PLDH) may be quantified by measuring the absorbance of the reagent/hemolysate mixture in a spectrophotometer (e.g. Shimadzu Co. model 160) set at wavelength of about 600 nm. In an alternative procedure, the same materials listed above may be placed on a solid support media (e.g. Whatman grade no.3 filter paper) to determine if a color change is produced.

EXAMPLE 4

In this Example, 0.1 microliters of hemolysate prepared as described above in Example 1 was combined with 1.0 ml of reagent consisting of 0.05M, pH 9.0 TRIS buffer, 10.0 $\mu$M APAD, and 1.0 mM lithium lactate. Parasitized and non-parasitized samples were made. The reagent and hemolysate mixtures were then immediately examined with a hand-held, long wave ultraviolet lamp capable of providing long wavelength ultraviolet light with excitation at about 375 nm and emission at about 440-480 nm. In the alternative, the mixture was examined in a fluorometer known in the art equipped to measure quantitatively the production of APADH. Using either procedure, the parasitized sample demonstrated pronounced fluorescence, while the non-parasitized sample did not.

EXAMPLE 5

In this example, a 2$\mu$L sample of hemolysate (parasitized or non-parasitized, prepared as under Example 1 above) was separated into LDH isoenzymes using a Beckman LD isoenzyme electrophoresis kit. Any similar electrophoresis apparatus is acceptable. The isoenzyme bands are visualized using the substrates provided in the Beckman kit. However, the distinct parasite isoenzyme band can be selectively and uniquely visualized by substituting for the NAD substrate reagent (kit reagent), the APAD substrate reagent described hereafter. The APAD substrate reagent consists of 0.1M, pH 9.0 Tris buffer, 5 mM APAD (6.81 mg), 200 mM lithium lactate (48.44 mg), 2.4 mM nitro blue tetrazolium (4 mg) and 0.33 mM phenazine methosulfate (0.2 mg) in a 2 ml volume. Except for the substitution of the APAD substrate reagent, the Beckman kit instructions were followed. The results (FIG. 3) clearly indicate that pLDH and erythrocyte LDH may readily be distinguished with the invention, thereby allowing malaria infections to be rapidly diagnosed.

FIGS. 3A and 3B show an electrophorogram of uninfected control human blood (C) and parasite infected blood (P) stained with either the reagent provided with the Beckman kit or the reagent described in this patent. With the Beckman kit reagent (FIG. 3A) there are three bands with uninfected blood (C) and four bands with infected (P) blood. With the APAD reagent there are no stained control bands. The one isoenzyme band stained with the APAD reagent is from the malaria parasite (P) infected blood. This confirms that this coenzyme (APAD) is specific for the parasite lactic acid dehydrogenase (PLDH).

The present invention represents a highly accurate and effective method for diagnosing human malaria infections. The invention is capable of detecting at least a 0.01% parasitemia. Also, it does not require the use of complex analytical equipment, nor does it require trained technical personnel. Accordingly, the present invention represents an advance in malaria diagnostic technology for which there has been a long felt need.

Having herein described a preferred embodiment of the invention, it is anticipated that suitable modifications may be made thereto by individuals skilled in the art within the scope of the invention. Thus, the invention shall only be construed in accordance with the following claims:

What is claimed is:

1. A diagnostic method for the detection of *Plasmodium falciparum* in human subjects comprising the steps of:
    obtaining a blood sample from a human test subject;
    combining said blood sample with a diagnostically effective amount of a reagent comprising 3-acetyl pyridine adenine dinucleotide, at least one buffer, and at least one substrate selected from the group consisting of a lactate salt and lactic acid; and
    analyzing said blood sample after said combining with said reagent to determine if said 3-acetyl pyridine adenine dinucleotide has been enzymatically reduced, the reduction of said 3-acetyl pyridine adenine dinucleotide indicating that said test subject is infected with *Plasmodium falciparum*.

2. The method of claim 1 wherein said blood sample comprises a composition selected from the group consisting of a blood hemolysate and blood serum.

3. The method of claim 1 wherein said blood sample and said reagent are combined in a sample:reagent volume ratio of about 1:1 to about 1:300.

4. The method of claim 1 wherein said reagent has a pH of about 8.0 to about 10.0.

5. The method of claim 1 wherein said lactate salt is selected from the group consisting of lithium lactate, magnesium lactate, sodium lactate, and calcium lactate.

6. The method of claim 1 wherein said reagent comprises about 0.01 mM–10 mM 3-acetyl pyridine adenine dinucleotide, about 0.02–1.0M buffer, and about 0.01–500 mM substrate.

7. The method of claim 1 wherein said analyzing of said blood sample comprises the steps of:
    placing said sample in an ultraviolet spectrophotometer; and
    reading said sample in said ultraviolet spectrophotometer with the wavelength set at about 340–380 nm, the presence of absorption at this wavelength indicating that said test subject is infected with *Plasmodium falciparum*.

8. The method of claim 1 wherein said analyzing of said blood sample comprises the steps of:
    providing at least one chemical detecting agent, said chemical detecting agent producing a visible color change in the presence of reduced 3-acetyl pyridine adenine dinucleotide;
    combining said blood sample with said chemical detecting agent; and
    determining if said visible color change has taken place, said visible color change indicating that said test subject is infected with *Plasmodium falciparum*.

9. The method of claim 1 wherein aid analyzing of said blood sample comprises the step of:
    providing a source of long wavelength ultraviolet light with excitation at about 375 nm and emission at about 440–480 nm;
    applying said ultraviolet light from said source onto said blood sample;
    observing said sample to determine if it visually fluoresces, the fluorescence of said sample indicating that said test subject is infected with *Plasmodium falciparum*.

10. A diagnostic method for the detection of *Plasmodium falciparum* in human subjects comprising the steps of:
    obtaining a blood sample from a human test subject;
    combining said blood sample with a reagent comprising about 0.01–10 mM 3-acetyl pyridine adenine dinucleotide, about 0.02–1.0M of at least one buffer, and about 0.01–500 mM of at least one substrate selected from the group consisting of a lactate salt and lactic acid, said blood sample being combined with said reagent in a blood sample:reagent volume ratio of about 1:1 to about 1:300; and
    analyzing said blood sample after said combining with said reagent to determine if said 3-acetyl pyridine adenine dinucleotide has been enzymatically reduced, the reduction of said 3-acetyl pyridine adenine dinucleotide indicating that said test subject is infected with *Plasmodium falciparum*.

11. The method of claim 10 wherein said reagent has a pH of about 8.0 to about 10.0.

12. The method of claim 10 wherein said lactate salt is selected from the group consisting of lithium lactate, magnesium lactate, sodium lactate, and calcium lactate.

13. The method of claim 1 further comprising the step of electrophoresing said blood sample after said obtaining thereof, said combining of said blood sample with said reagent comprising staining the electrophoresed blood sample with said reagent; and said analyzing of said blood sample comprising observing the stained electrophoresed blood sample to determine if a distinct, visible PLDH isoenzyme band exists, the presence of said isoenzyme band indicating that said test subject is infected with *Plasmodium falciparum*.

14. The method of claim 10 wherein said analyzing of said blood sample comprises the steps of:
    providing at least one chemical detecting agent, said chemical detecting agent producing a visible color change in the presence of reduced 3-acetyl pyridine adenine dinucleotide;
    combining said blood sample with said chemical detecting agent; and
    determining if said visible color change has taken place, said visible color change indicating that said test subject is infected with *Plasmodium falciparum*.

15. The method of claim 10 wherein said analyzing of said blood sample comprises the step of:

providing a source of long wavelength ultraviolet light with excitation of about 375 nm and emission at about 440–480 nm;

applying said ultraviolet light from said source onto said blood sample; and observing said sample to determine if it visually fluoresces, the fluorescence of said sample indicating that said test subject is infected with *Plasmodium falciparum*.

* * * * *